(12) United States Patent
Snow

(10) Patent No.: US 10,568,611 B2
(45) Date of Patent: Feb. 25, 2020

(54) FLUSH CUT BIOPSY NEEDLE ASSEMBLY AND METHOD OF USE

(71) Applicant: Merit Medical Systems, Inc., South Jordan, UT (US)

(72) Inventor: Jeremy W. Snow, South Jordan, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 116 days.

(21) Appl. No.: 14/598,457

(22) Filed: Jan. 16, 2015

(65) Prior Publication Data

US 2015/0201917 A1    Jul. 23, 2015

Related U.S. Application Data

(60) Provisional application No. 61/928,865, filed on Jan. 17, 2014.

(51) Int. Cl.
*A61B 10/02* (2006.01)

(52) U.S. Cl.
CPC .. *A61B 10/0266* (2013.01); *A61B 2010/0208* (2013.01)

(58) Field of Classification Search
None
See application file for complete search history.

(56) References Cited

U.S. PATENT DOCUMENTS

| | | | |
|---|---|---|---|
| 4,785,826 A * | 11/1988 | Ward | A61B 10/025 30/174 |
| 4,946,445 A | 8/1990 | Lynn | |
| 5,172,702 A | 12/1992 | Leigh et al. | |
| 5,368,574 A | 11/1994 | Antonacci et al. | |
| 5,601,572 A | 2/1997 | Middleman et al. | |
| 5,655,542 A | 8/1997 | Weilandt | |
| 5,788,651 A | 8/1998 | Weilandt | |
| 5,800,389 A | 9/1998 | Burney et al. | |
| 5,842,999 A | 12/1998 | Pruitt et al. | |
| D418,223 S | 12/1999 | Phipps et al. | |
| D428,150 S | 7/2000 | Ruf et al. | |
| 6,126,617 A | 10/2000 | Weilandt et al. | |
| 6,146,338 A | 11/2000 | Gardeski et al. | |

(Continued)

FOREIGN PATENT DOCUMENTS

| AT | 366546 | 6/1976 |
|---|---|---|
| EP | 0583144 | 2/1994 |

(Continued)

OTHER PUBLICATIONS

International Search Report and Written Opinion dated Jun. 23, 2015 for PCT/US2013/076418.

(Continued)

*Primary Examiner* — Matthew Kremer

(74) *Attorney, Agent, or Firm* — Stoel Rives LLP

(57) ABSTRACT

A biopsy needle assembly configured for use with a tissue biopsy device is disclosed. The biopsy needle assembly may be configured to be advanced to a predetermined tissue sample, sever the tissue sample, and extract the tissue sample from a body tissue of a patient. The biopsy needle assembly may be further configured to minimize or eliminate the length of dead space at or adjacent a position of the tissue sample extraction.

22 Claims, 8 Drawing Sheets

(56) References Cited

U.S. PATENT DOCUMENTS

| | | |
|---|---|---|
| 6,196,978 B1 | 3/2001 | Weilandt et al. |
| 6,322,523 B2 | 11/2001 | Weilandt et al. |
| 6,340,356 B1 | 1/2002 | Navia et al. |
| D457,955 S | 5/2002 | Bilitz |
| 6,419,641 B1 | 7/2002 | Mark et al. |
| D463,555 S | 9/2002 | Etter et al. |
| 6,488,662 B2 | 12/2002 | Sirimanne |
| 6,497,687 B1 | 12/2002 | Blanco |
| 6,656,195 B2 * | 12/2003 | Peters ............ A61B 17/32002 606/159 |
| D490,152 S | 5/2004 | Myall et al. |
| 7,041,065 B2 | 5/2006 | Weilandt et al. |
| 7,247,160 B2 | 7/2007 | Seiler et al. |
| D571,009 S | 6/2008 | Smith et al. |
| 7,470,237 B2 | 12/2008 | Beckman et al. |
| D586,916 S | 2/2009 | Faulkner et al. |
| D598,543 S | 8/2009 | Vogel et al. |
| 7,608,048 B2 | 10/2009 | Goldenberg |
| D612,044 S | 3/2010 | Scheibe |
| D612,051 S | 3/2010 | Ruf |
| D619,251 S | 7/2010 | Justiniano-Garcia et al. |
| D628,293 S | 11/2010 | Ruf |
| 8,137,317 B2 | 3/2012 | Osypka |
| 9,392,998 B2 | 7/2016 | Snow |
| 2001/0009979 A1 | 7/2001 | Weilandt et al. |
| 2003/0153842 A1 | 8/2003 | Lamoureux et al. |
| 2004/0054377 A1 | 3/2004 | Foster et al. |
| 2004/0133124 A1 | 7/2004 | Bates et al. |
| 2004/0215103 A1 | 10/2004 | Meuller, Jr. et al. |
| 2005/0054947 A1 | 3/2005 | Goldenberg |
| 2005/0125017 A1 | 6/2005 | Kudrna et al. |
| 2006/0085019 A1 | 4/2006 | Cote et al. |
| 2006/0195175 A1 | 8/2006 | Bregulla |
| 2006/0211992 A1 | 9/2006 | Prosek |
| 2006/0224082 A1 | 10/2006 | Vetter et al. |
| 2007/0027407 A1 | 2/2007 | Miller |
| 2007/0078472 A1 | 4/2007 | Singh |
| 2007/0142744 A1 | 6/2007 | Provencher |
| 2007/0179403 A1 | 8/2007 | Heske et al. |
| 2007/0250037 A1 | 10/2007 | Brimhall et al. |
| 2008/0051820 A1 | 2/2008 | Gong et al. |
| 2008/0300507 A1 | 2/2008 | Figueredo et al. |
| 2008/0161720 A1 | 7/2008 | Nicoson |
| 2008/0200833 A1 | 8/2008 | Hardin et al. |
| 2008/0228104 A1 | 9/2008 | Uber et al. |
| 2008/0281223 A1 | 11/2008 | Goldenberg |
| 2009/0118704 A1 | 5/2009 | Sharrow et al. |
| 2009/0143698 A1 | 6/2009 | Janssens |
| 2009/0259200 A1 | 10/2009 | Lampropoulos et al. |
| 2009/0275966 A1 * | 11/2009 | Mitusina .......... A61B 17/32002 606/171 |
| 2009/0299220 A1 | 12/2009 | Field et al. |
| 2010/0010526 A1 * | 1/2010 | Mitusina .......... A61B 17/32002 606/171 |
| 2010/0130887 A1 | 5/2010 | Selis |
| 2010/0168773 A1 | 7/2010 | Funderburk et al. |
| 2010/0179484 A1 | 7/2010 | Carrez et al. |
| 2011/0251631 A1 | 10/2011 | Trees et al. |
| 2012/0220894 A1 | 8/2012 | Melsheimer |
| 2012/0226101 A1 | 9/2012 | Tinkham et al. |
| 2013/0131548 A1 | 5/2013 | McGhit et al. |
| 2013/0150795 A1 | 6/2013 | Snow |
| 2014/0100479 A1 | 4/2014 | Tripp et al. |
| 2014/0171826 A1 | 6/2014 | Lampropoulos et al. |
| 2014/0207021 A1 | 7/2014 | Snow |
| 2014/0276453 A1 | 9/2014 | Woehr |
| 2015/0045828 A1 | 2/2015 | McArthur et al. |
| 2015/0094751 A1 | 4/2015 | Chen et al. |
| 2015/0201917 A1 | 7/2015 | Snow |
| 2016/0089208 A1 * | 3/2016 | Vetter ................ A61B 10/0266 606/130 |

FOREIGN PATENT DOCUMENTS

| | | |
|---|---|---|
| EP | 0966920 | 12/1999 |
| EP | 1661521 | 5/2006 |
| JP | 2005511989 | 4/2005 |
| JP | 2008510596 | 4/2008 |
| JP | 2008100054 | 5/2008 |
| JP | 2008104856 | 5/2008 |
| JP | 2009279096 | 12/2009 |
| WO | WO1996/22733 | 8/1996 |
| WO | WO1999/44505 | 9/1999 |
| WO | WO2006/013389 | 2/2006 |

OTHER PUBLICATIONS

International Search Report and Written Opinion dated Apr. 30, 2015 for PCT/US2015/012002.
International Search Report and Written Opinion dated Jan. 16, 2015 for PCT/US2015/011746.
U.S. Appl. No. 29/495,581, filed Jul. 2, 2014, Snow.
U.S. Appl. No. 14/600,660, filed Jan. 20, 2015, Snow.
Shuttle® and CT-Core® Semi-Automatic devices; Updated to the website between Nov. 8, 2012-Jan. 24, 2013. Accessed website on Jun. 27, 2014 at http://www.vigeohealthcare.com/gb/int_radiplogy.html.
International Search Report and Written Opinion dated May 1, 2014 for PCT/US2014/012043.
International Search Report and Written Opinion dated Apr. 3, 2014 for PCT/US2013/076418.
Office Action dated Jul. 5, 2017 for U.S. Appl. No. 14/134,280.
Office Action dated Aug. 7, 2017 for U.S. Appl. No. 14/600,660.
Extended European Search Report dated Aug. 26, 2016 for EP13863978.6.
Office Action dated Jun. 1, 2016 for U.S. Appl. No. 14/134,280.
Office Action dated Dec. 23, 2016 for U.S. Appl. No. 14/134,280.
International Preliminary Report dated Jul. 19, 2016 for PCT/US2015/011746.
European Search Report dated Aug. 17, 2017 for EP15737182.4.
Office Action dated Jan. 17, 2018 for U.S. Appl. No. 14/134,280.
European Search Report dated Nov. 13, 2017 for EP15740963.2.
Office Action dated Feb. 5, 2018 for U.S. Appl. No. 14/600,660.
Office Action dated Mar. 26, 2018 for U.S. Appl. No. 15/184,551.
Office Action dated Sep. 5, 2018 for U.S. Appl. No. 14/600,660.
Office Action dated Oct. 9, 2018 for U.S. Appl. No. 15/184,551.
Office Action dated Oct. 31, 2018 for U.S. Appl. No. 14/134,280.
Office Action dated Jan. 18, 2019 for U.S. Appl. No. 14/600,660.
Office Action dated Feb. 26, 2019 for U.S. Appl. No. 15/184,551.
Office Action dated Apr. 2, 2019 for U.S. Appl. No. 14/134,280.
Notice of Allowance dated Oct. 23, 2019 for U.S. Appl. No. 15/184,551.
Office Action dated Oct. 11, 2019 for U.S. Appl. No. 14/134,280.
Office Action dated Jul. 31, 2019 for U.S. Appl. No. 14/600,660.

* cited by examiner

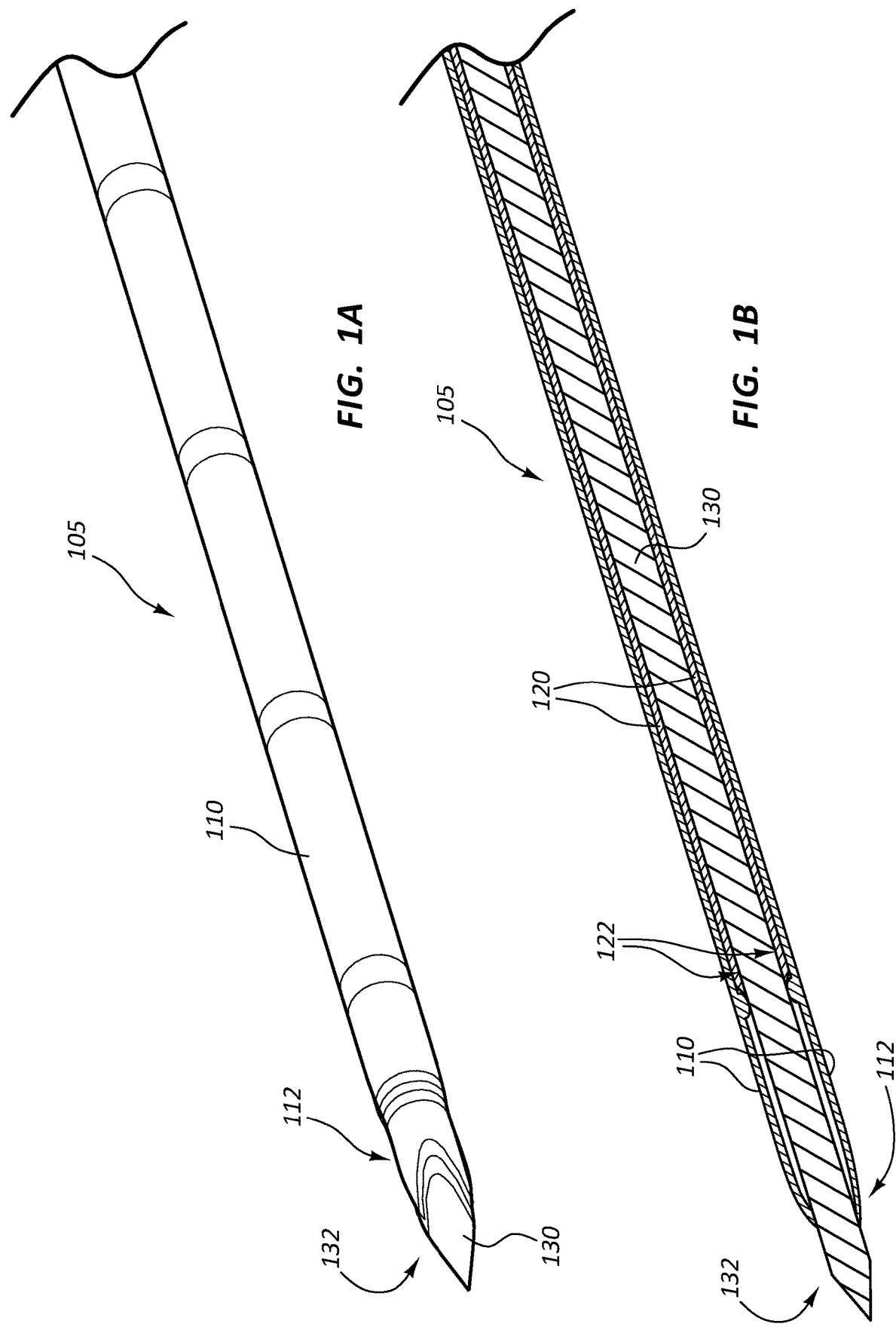

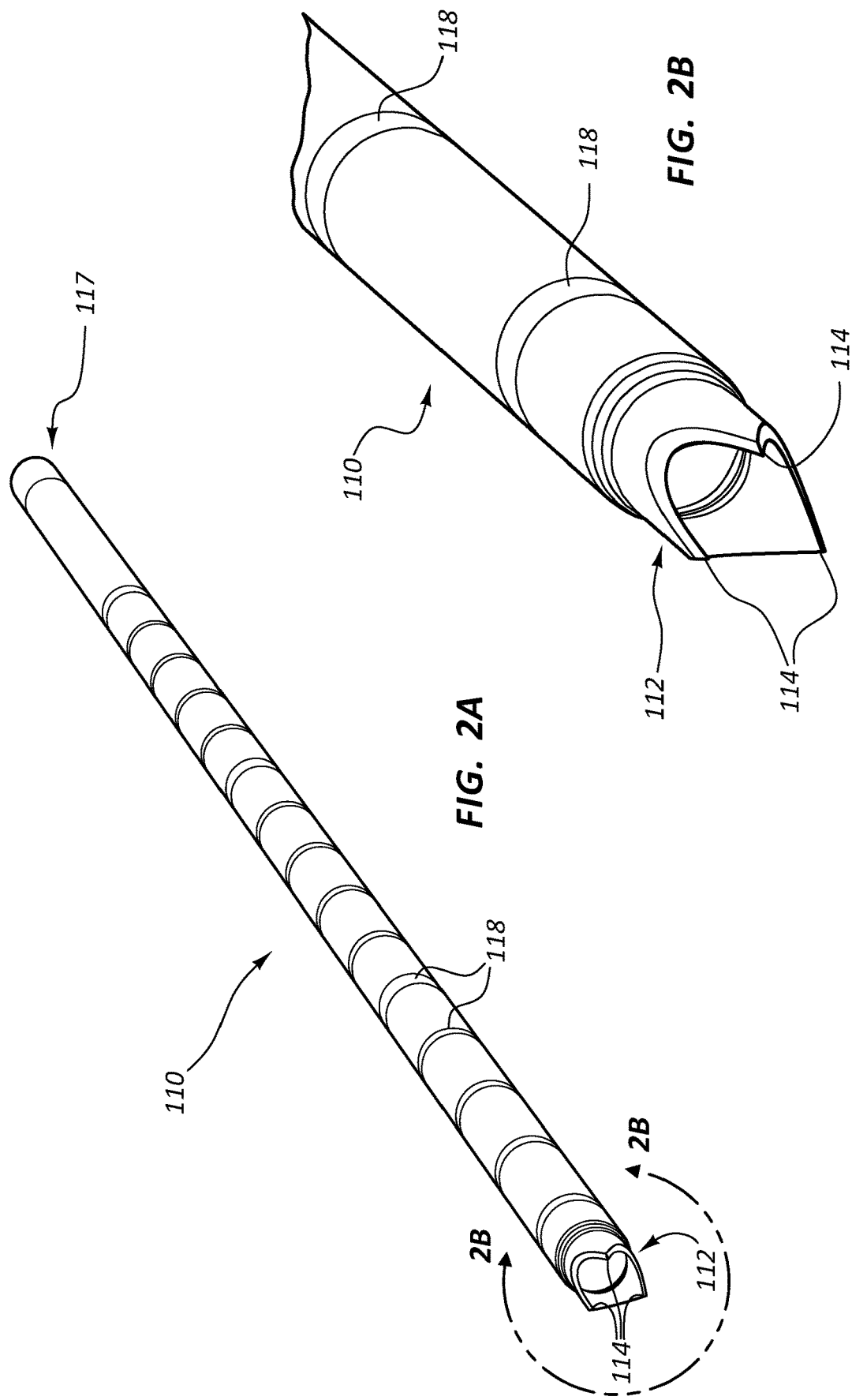

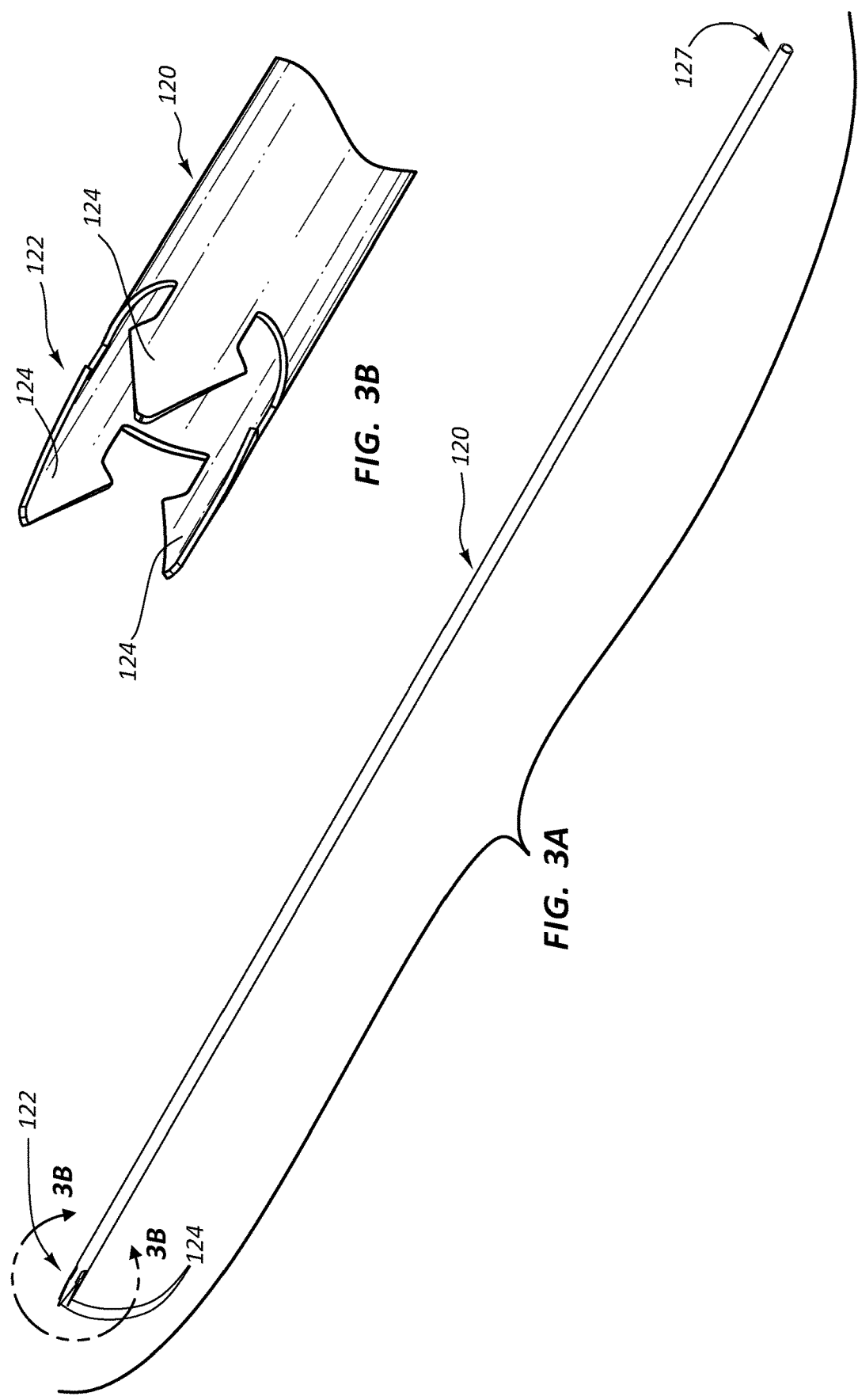

FLUSH CUT BIOPSY NEEDLE ASSEMBLY AND METHOD OF USE

RELATED APPLICATION

This application claims priority to U.S. Provisional Application No. 61/928,865 filed Jan. 17, 2014, titled FLUSH CUT BIOPSY NEEDLE ASSEMBLY AND METHOD OF USE, the entire contents of which are hereby incorporated by reference.

TECHNICAL FIELD

The present disclosure relates generally to medical devices. More specifically, the present disclosure relates to biopsy needle assemblies configured for use with tissue biopsy devices, including needle assemblies configured to decrease, minimize, or eliminate dead space at or adjacent a tissue sample collection site.

BRIEF DESCRIPTION OF THE DRAWINGS

The embodiments disclosed herein will become more fully apparent from the following description and appended claims, taken in conjunction with the accompanying drawings. The drawings depict only typical embodiments, which embodiments will be described with additional specificity and detail in connection with the drawings in which:

FIG. 1A is a perspective view of a portion of a biopsy needle assembly.

FIG. 1B is a cross-sectional view of the portion of the biopsy needle assembly of FIG. 1A.

FIG. 2A is a perspective view of an outer tubular member of the biopsy needle assembly of FIGS. 1A and 1B.

FIG. 2B is a detail view of a distal end portion of the outer tubular member of FIG. 2A taken through line 2B.

FIG. 3A is a perspective view of a cutting member of the biopsy needle assembly of FIG. 1B.

FIG. 3B is a detail view of a distal end portion of the cutting member of FIG. 3A taken through line 3B.

DETAILED DESCRIPTION

Figures 3C, 3D:
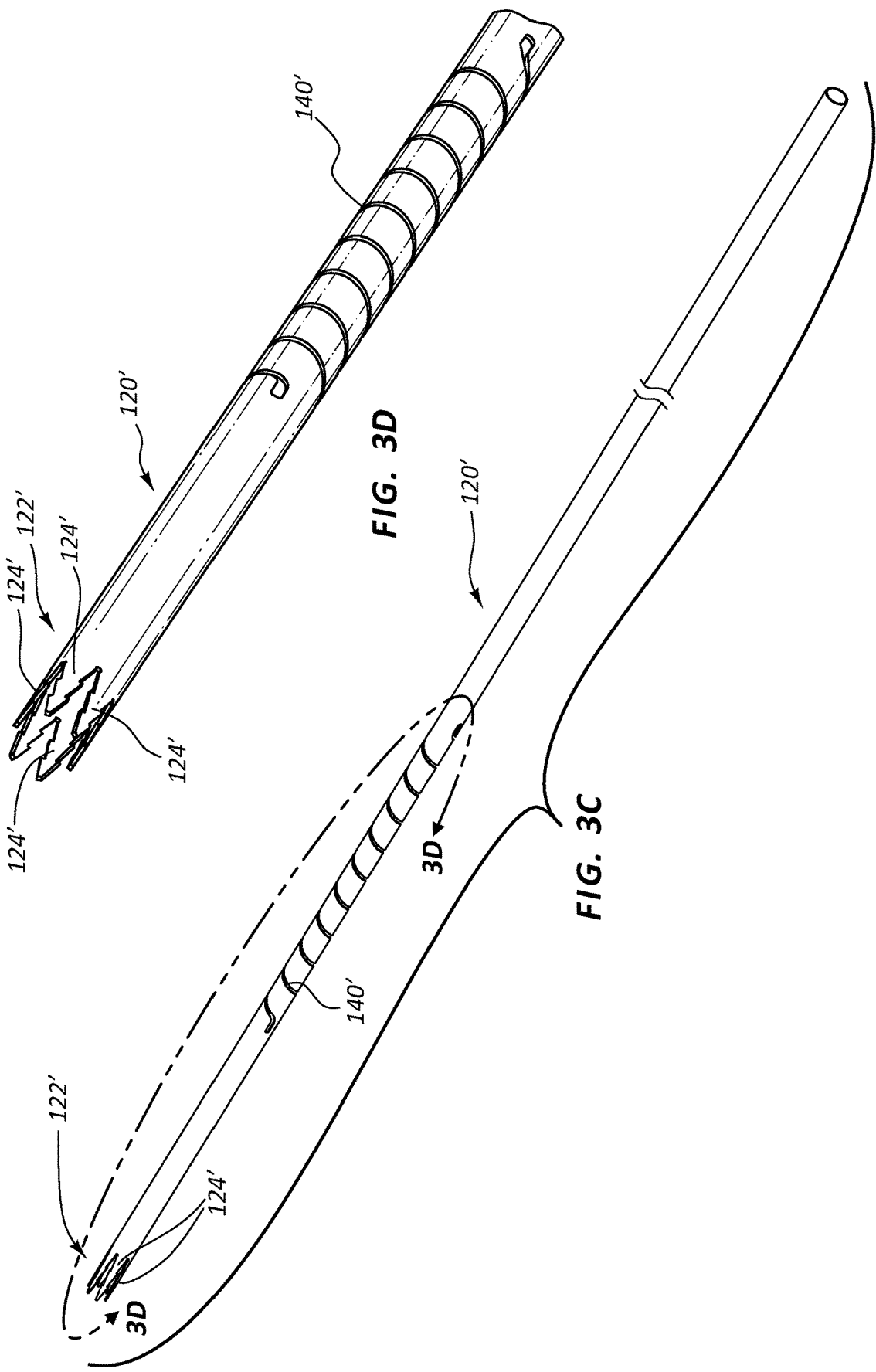
FIG. 3C is a perspective view of another embodiment of a cutting member of a biopsy needle assembly analogous to the biopsy needle assembly of FIG. 1B.
FIG. 3D is a detail view of a distal end portion of the cutting member of FIG. 3C taken through line 3D.

Tissue biopsy devices may be configured to retrieve tissue samples from various locations within a patient's body. For example, a biopsy device may comprise a biopsy needle assembly, or needle assembly, including tubular members, cutting members, styli, cannula, and/or other components configured to access and sever a tissue sample. The needle assembly may be advanced to a location within the body through the skin of the patient (percutaneous access) or may be advanced through a body lumen or other structure. Furthermore, a biopsy device may comprise a handle or actuator configured to displace or deflect at least a portion of the needle assembly such that the needle assembly severs the targeted tissue sample.

It will be readily understood that the components of the embodiments as generally described and illustrated in the Figures herein could be arranged and designed in a wide variety of different configurations. Thus, the following more detailed description of various embodiments, as represented in the Figures, is not intended to limit the scope of the disclosure, but is merely representative of various embodiments. While the various aspects of the embodiments are presented in drawings, the drawings are not necessarily drawn to scale unless specifically indicated.

The phrases "connected to" and "coupled to" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The directional terms "proximal" and "distal" are used herein to refer to opposite locations on a medical device. The proximal end of the device is defined as the end of the device closest to the practitioner when the device is in use by the practitioner. The distal end is the end opposite the proximal end, along the longitudinal direction of the device, or the end furthest from the practitioner.

FIG. 1A is a perspective view of a portion of a biopsy needle assembly 105, and FIG. 1B is a cross-sectional view of the portion of the biopsy needle assembly 105 of FIG. 1A. As illustrated, the needle assembly 105 can comprise an outer tubular member 110 comprising a distal end portion 112. In some embodiments, the outer tubular member 110, and/or the distal end portion 112 of the outer tubular member 110, may be configured to cut or sever a first portion of a tissue sample. For example, advancement of the outer tubular member 110 through a tissue sample may core or cut the tissue sample and create a tube-like cut into the tissue, as further discussed below.

Referring to FIG. 1B, the biopsy needle assembly 105 can further comprise a cutting member 120, wherein the cutting member 120 may be slidably disposed within the outer tubular member 110. As depicted, the cutting member 120 can comprise a distal end portion 122. In certain embodiments, the distal end portion 122 of the cutting member 120 may be configured to displace inward to cut or sever a distal end portion, or second portion, of the tissue sample. For example, a practitioner, such as a medical doctor, may identify a tissue in a patient to be extracted or sampled from the patient (i.e., for further analysis). The outer tubular member 110 can core or cut into the identified tissue sample and create a tube-like cut into the tissue, thus cutting or severing a first portion of the tissue sample. Subsequently, in some embodiments, the cutting member 120 can be configured to cut or sever a distal end of the tissue sample, or second portion of the tissue sample. Upon severing each of the first and the second portions of the tissue sample, the tissue sample may be separated from surrounding body tissue and the tissue sample may be extracted or removed from the patient, at least in part, by the biopsy needle assembly 105. In other embodiments, the cutting or severing of the first portion of the tissue sample may be performed subsequent to the cutting or severing of the second portion of the tissue sample.

Referring again to FIGS. 1A and 1B, the needle assembly 105 can further comprise a stylet 130, or trocar, wherein the cutting member 120 may be slidably disposed around the stylet 130. The stylet 130 can also comprise a distal end portion 132. In some embodiments, the stylet 130, and/or the distal end portion 132 of the stylet 130, may be configured to facilitate advancement or displacement of the needle assembly 105 through body tissue to a position at or adjacent an identified tissue sample. For example, a practitioner can advance the stylet through the skin and/or tissue of a patient to a position at or adjacent to the site of an identified tissue sample. As the stylet is advanced, the stylet may displace the skin and/or tissue such that a pathway is generated through the skin and/or tissue that may ease advancement of other components of the needle assembly 105 to the position at or adjacent to the site of the tissue sample.

FIG. 2A is a perspective view of the outer tubular member 110 of FIGS. 1A and 1B, and FIG. 2B is a detail view of the distal end portion 112 of the outer tubular member 110 of FIG. 2A taken through line 2B. The outer tubular member 110 can comprise the distal end portion 112 and a proximal end portion 117. The outer tubular member 110 and/or the distal end portion 112 of the outer tubular member 110 may be configured to sever the first portion of the tissue sample. For example, the distal end portion 112 of the outer tubular member 110 may generate or make a tube-shaped cut into or through a body tissue.

The distal end portion 112 of the outer tubular member 110 of FIGS. 2A and 2B comprises a plurality of points 114, the points 114 forming a cutting or penetrating edge. The cutting or penetrating edge may be sharp such that the outer tubular member 110, and/or the distal end portion 112 of the outer tubular member 110, is configured to cut or sever at least a portion of the tissue sample. Other cutting arrangements and mechanisms are also contemplated. For example, the distal end portion 112 of the outer tubular member 110 may comprise an annular blade or sharpened edge configured to cut or sever tissue. In the illustrated embodiment, the distal end portion 112 of the outer tubular member 110 comprises three points 114. In other embodiments, the distal end portion 112 of the outer tubular member 110 may comprise one or two points 114, while in yet other embodiments, the distal end portion 112 of the outer tubular member 110 may comprise four, five, six, or more points 114. Distal end portions 112 of outer tubular members 110 comprising any number of points 114 are within the scope of this disclosure.

In some embodiments, at least a portion of the outer tubular member 110, or the distal end portion 112 of the outer tubular member 110, may be configured to allow or permit the outer tubular member 110 to more easily advance or be displaced through the body tissue. At least a portion of the outer tubular member 110, or the distal end portion 112 of the outer tubular member 110, may also be configured to decrease or limit the effect or impact of displacing or advancing the needle assembly into the body tissue of the patient.

Also, as illustrated, the outer tubular member 110 can comprise a plurality of indicia 118 configured to indicate to the practitioner a distance that the outer tubular member 110 has advanced into a body tissue (for clarity not all indicia 118 are labeled). For example, each indicium 118 may be positioned 1 cm apart; thus, if the practitioner displaces the outer tubular member 110 into a body tissue up to the third indicia 118 from the distal end portion 112 of the outer tubular member 110, it may indicate to the practitioner that approximately 3 cm of the outer tubular member 110 has been displaced into the body tissue. In some embodiments, the indicia 118 may comprise a plurality of substantially evenly spaced annular lines, marks, or grooves on an outside surface of the outer tubular member 110. In certain embodiments, the indicia 118 may comprise a plurality of tick marks or the indicia may not be evenly spaced. Embodiments of any configuration of indicia are contemplated.

A portion or portions of at least one of the components of the biopsy needle assembly, including, but not limited to, the outer tubular member 110, the indicia 118, the cutting member, and/or the stylet, may also comprise a radiopaque material and/or an echogenic material. A radiopaque material (for example, in combination with a fluoroscope) may aid the practitioner in directing or displacing the needle assembly to a desired or predetermined position within the body tissue of the patient. Bismuth, gold, or other radiopaque materials alone, or in combination, may be used. An echogenic material (for example, in combination with ultrasound) may analogously aid the practitioner in directing or displacing the needle assembly to a desired or predetermined position within the body tissue of the patient. Surface disruptions such as texturing, grooves, dimples, or a combination of materials may also be used.

FIG. 3A is a perspective view of the cutting member 120 of FIG. 1B, and FIG. 3B is a detail view of the distal end portion 122 of the cutting member 120 of FIG. 3A taken through line 3B. As depicted, the cutting member 120 may comprise a lumen along at least a portion of a length of the cutting member 120. The cutting member 120 can further comprise the distal end portion 122 and a proximal end portion 127. In some embodiments, the cutting member 120, and/or the distal end portion 122 of the cutting member 120, may be configured to cut or sever the distal end portion, or second portion, of the tissue sample, as described above. In some other embodiments, at least a portion of the distal end portion 122 of the cutting member 120 may be configured to displace inward to cut or sever the distal end portion, or second portion, of the tissue sample. For example, as stated above, the outer tubular member 110 may generate a tube-like cut into the body tissue, severing the first portion of the tissue sample, and the cutting member 120 may be configured to cut or sever the tissue sample at a distal end of the tissue sample, severing the second portion of the tissue sample, at or adjacent a distal end of the tube-like cut made by the outer tubular member 110. For example, the cutting member 120 may be configured to cut or sever the distal end portion, or second portion, of the tissue sample at the same longitudinal position as the distal end of the tube-like cut made by the outer tubular member 110. In other embodiments, the cutting member 120 may be configured to cut or sever the distal end portion, or second portion, of the tissue sample at a position less than 5 mm, less than 4 mm, less than 3 mm, less than 2 mm, or less than 1 mm from the distal end of the tube-like cut made by the outer tubular member 110. In various embodiments, the cutting member 120 may be configured to cut or sever the distal end portion, or second portion, of the tissue sample at a clinically relevant position from the distal end of the tube-like cut made by the outer tubular member 110. The cutting member 120 may also be configured to cut or sever the second portion of the tissue sample at other positions relative to the distal end of the tube-like cut made by the outer tubular member 110.

With continued reference to FIGS. 3A and 3B, the cutting member 120 may comprise a plurality of sectioning elements 124. In some embodiments, the cutting member 120 may comprise one or more sectioning elements 124. In various embodiments, the sectioning elements 124 may be coupled to the cutting member 120. In some configurations, the sectioning elements 124 and the cutting member 120 may be integrally formed from a single piece of material. In certain embodiments, at least one of the sectioning elements 124 may comprise a sharp distal portion. At least one of the sectioning elements 124 may also comprise at least one sharp lateral edge portion. In some embodiments, the at least one sharp lateral edge portion may be angled. As depicted in FIG. 3B, the sectioning elements 124 can be spade- or shovel-shaped. Such a configuration of the one or more of the sectioning elements 124 may facilitate the cutting or severing of body tissue by the sectioning elements 124. The shape of the sectioning elements 124 may be configured such that the sectioning elements 124 may be simultaneously, or substantially simultaneously, inwardly displaced toward each other to sever the second portion of the tissue sample. Interaction with other components of a biopsy device may be configured to inwardly displace the sectioning elements 124. For example, and as further detailed below in connection with FIGS. 4A and 4B, interaction between the sectioning elements 124 and one or more portions of the outer tubular member 110 may cause the sectioning elements 124 to displace inwardly.

Referring again to FIGS. 3A and 3B, at least a portion of at least one of the sectioning elements 124 may be elastically deformable radially inward toward a central axis of the cutting member 120. In some embodiments, at least a portion of one of the sectioning elements 124, or at least one of the sectioning elements 124, may comprise a super elastic alloy, such as nitinol, for example. Displacement of at least a portion of at least one of the sectioning elements 124 toward the central axis of the cutting member 120 may be configured to sever the second portion of the tissue sample. In certain embodiments, a portion of each of the sectioning elements 124 may be configured to displace toward the central axis of the cutting member 120 to sever the second portion of the tissue sample. The cutting member 120 may be further configured to sever the second portion of the tissue sample at or adjacent a distal-most point of the distal end portion of the outer tubular member. For example, the cutting member 120 may be configured to cut or sever the second portion of the tissue sample at a position less than 5 mm, less than 4 mm, less than 3 mm, less than 2 mm, or less than 1 mm from the distal-most point of the distal end portion of the outer tubular member. The cutting member 120 may also be configured to cut or sever the second portion of the tissue sample at the same longitudinal position as the distal-most point of the distal end portion of the outer tubular member. The cutting member 120 may also be configured to cut or sever the second portion of the tissue sample at other positions relative to the distal-most point of the distal end portion of the outer tubular member.

The components of the present disclosure may be configured to minimize or eliminate dead space, as further detailed in connection with FIGS. 4A and 4B below. Some biopsy devices may comprise one or more cutting members that are configured to cut or sever a body tissue of a patient. As such, a practitioner may advance the one or more cutting members into a body tissue, cutting or severing at least a portion of the tissue along a certain length, which may be termed a stroke length. Additionally, one or more of the cutting members may be configured to cut or sever a distal end of the tissue sample. The distal end of the tissue sample may be positioned proximal to a distal end of the stroke length. Thus, as described, the tissue sample length can be shorter than the stroke length. Consequently, there may be a gap or space between the distal end of the tissue sample and the distal end of the stroke length. Such a gap or space may be termed a dead space. The dead space may comprise tissue that is at least partially severed (i.e., by the initial advancement of the one or more cutting members into the body tissue) but that is positioned distal to the distal end of the tissue sample, and thus not extracted from the patient upon retraction of the needle assembly and/or the tissue sample from the body tissue. In other words, the dead space is body tissue that is at least partially cut or severed but that is not part of the tissue sample. Tissue at or adjacent the dead space may be damaged, and as such a practitioner may desire to minimize or avoid generating dead space.

In some instances, for example as described in the present disclosure, the structure and/or the form of the one or more cutting members of the biopsy device may be designed to minimize or eliminate a length or an amount of generated dead space. As stated, embodiments of the needle assembly of the current disclosure can be configured to minimize or eliminate the generation or production of dead space.

Minimizing or eliminating dead space may increase the precision with which a practitioner can extract a tissue sample and thus limit unwanted trauma to tissue around the sample site. For example, in some instances, a practitioner may identify or locate a tissue sample for removal or extraction from a patient. The identified tissue sample, however, may be positioned at or adjacent to a body component, tissue, or organ that the practitioner may desire or need to avoid cutting, piercing, severing, etc. The body component may include, but is not limited to, a vessel. A biopsy needle assembly that is configured to minimize or eliminate dead space may be utilized in such a circumstance or situation. At least a portion of a biopsy needle assembly, as disclosed herein, can be disposed at or adjacent the tissue sample; the needle assembly may sever and/or extract the tissue sample without cutting, piercing, or severing body components, such as vessels, which may be positioned at or adjacent the tissue sample.

FIG. 3C is a perspective view of another embodiment of a cutting member and FIG. 3D is a detail view of a distal end portion of the cutting member of FIG. 3C taken through line 3D that can, in certain respects, resemble components of the cutting member described in connection with FIGS. 3A and 3B. It will be appreciated that all the illustrated embodiments may have analogous features. Accordingly, like features are designated with like reference numerals, with the reference numerals appended with the prime symbol ('). For instance, the distal end portion is designated as "122" in FIGS. 3A and 3B, and an analogous distal end portion is designated as "122'" in FIGS. 3C and 3D. Relevant disclosure set forth above regarding similarly identified features thus may not be repeated hereafter. Moreover, specific features of the cutting member and related components shown in FIGS. 3A and 3B may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the cutting member of FIGS. 3C and 3D. Any suitable combination of the features, and variations of the same, described with respect to the cutting member and components illustrated in FIGS. 3A and 3B can be employed with the cutting member and components of FIGS. 3C and 3D, and vice versa. This pattern of disclosure applies equally to further embodiments depicted in subsequent figures and described hereafter.

FIG. 3C is a perspective view of a cutting member 120', analogous to the cutting member 120 of FIG. 3A, and FIG. 3D is a detail view of a distal end portion 122' of the cutting member 120' of FIG. 3C taken through line 3D. As depicted, the cutting member 120' may comprise a lumen along at least a portion of a length of the cutting member 120'. The cutting member 120' may also comprise a plurality of sectioning elements 124'. Additionally, the cutting member 120' may comprise one or more spiral cuts 140' disposed along at least a portion or portions of the length of the cutting member 120'. In the illustrated embodiment, the spiral cut 140' is disposed along at least a portion of the length of the cutting member 120' at a position proximal to the sectioning elements 124'. In various embodiments, the cutting member 120' may comprise a spiral cut 140' disposed proximal of the one or more sectioning elements 124'. In some embodiments, the spiral cut 140' may be disposed at a distance sufficiently proximal in relation to the sectioning elements 124' such that the spiral cut 140' does not, or does not substantially, interfere with or damage a tissue sample.

In some embodiments, the cutting member 120' may comprise one or more sectioning elements 124' (e.g., two, three, four, five, six, or more sectioning elements 124'). In the illustrated embodiment, the cutting member 120' comprises six sectioning elements 124'. As discussed above, the sectioning elements 124' may be coupled to the cutting member 120'. In some configurations, the sectioning elements 124' and the cutting member 120' may be integrally formed from a single piece of material. In certain embodiments, at least one of the sectioning elements 124' may comprise a sharp distal portion. As depicted in FIGS. 3C and 3D, the sectioning elements 124' can comprise a pointed or tapered distal portion. At least one of the sectioning elements 124' may also comprise at least one sharp lateral edge portion. In some embodiments, the at least one sharp lateral edge portion may be angled.

With continued reference to FIGS. 3C and 3D, the sectioning elements 124' can comprise a plurality of angled lateral edge portions. For example, the lateral edge portions of the section elements 124' may be serrated or notched. Such a configuration of the one or more sectioning elements 124' may facilitate the cutting or severing of body tissue by the sectioning elements 124'.

As discussed above with respect to the sectioning elements 124, the shape of the sectioning elements 124' may also be configured such that the sectioning elements 124' may be simultaneously, or substantially simultaneously, inwardly displaced toward each other to sever the second portion of the tissue sample. Interaction with other components of a biopsy device may also be configured to inwardly displace the sectioning elements 124'. For example, and as further detailed below in connection with FIGS. 4A and 4B, interaction between the sectioning elements 124' and one or more portions of the outer tubular member may cause the sectioning elements 124' to displace inwardly.

In some embodiments, the spiral cut 140' may extend completely through a wall of the cutting member 120'. In some other embodiments, the spiral cut 140' may only extend partially through the wall of the cutting member 120'. For example, the spiral cut 140' may form a groove along a portion of the length of the cutting member 120'. In yet other embodiments, one or more portions of the spiral cut 140' may extend completely through the wall of the cutting member 120' while one or more other portions of the spiral cut 140' may form a groove in the wall of the cutting member 120'.

In certain embodiments, disposition of the spiral cut 140' along the cutting member 120' can form a spring, or a spring-like portion, along the cutting member 120'. The spiral cut 140' may add or provide compliance or elasticity to the cutting member 120' and/or the biopsy needle assembly. For example, the spiral cut 140' may improve or increase tolerances of one or more of the components of the cutting member 120' and/or the biopsy needle assembly. Such improved tolerances may facilitate advancement or displacement of the cutting member 120' and/or the biopsy needle assembly through a body tissue. In various embodiments, the spiral cut 140' may absorb impact or shock to one or more of the cutting member 120', other components of the biopsy needle assembly, and/or the biopsy needle assembly. For example, upon advancement or displacement of at least a portion of the biopsy needle assembly through a body tissue of a patient, at least a portion of the spiral cut 140' may compress or be configured to compress (i.e., the spiral cut 140' may compress longitudinally, thus shortening the length of the cutting member 120'). In certain embodiments, the spiral cut 140' can be configured to longitudinally compress in response to relative displacement of the outer tubular member, or another component of the biopsy needle assembly, in relation to the cutting member 120'.

One or more forces may result in or cause compression of the spiral cut 140'. For example, inertia of the cutting member 120' as it is advanced into a body tissue can result in compression of the spiral cut 140'. Displacement of the cutting member 120' in relation to the outer tubular member and/or the stylet may also result in compression of the spiral cut 140'. For example, friction between an outside surface of the cutting member 120' and an inside surface of the outer tubular member may result in compression of the spiral cut 140'. Likewise, friction between an inside surface of the cutting member 120' and an outside surface of the stylet may also result in compression of the spiral cut 140'. Furthermore, force used to advance or displace the distal end portion 122' and/or the sectioning elements 124' of the cutting member 120' over or past the protrusions or annular ring of the outer tubular member can also result in compression of the spiral cut 140'.

Additionally, at least a portion of the spiral cut 140' may rotate, or be configured to rotate, upon compression of the spiral cut 140'. Rotation of the spiral cut 140' may also cause or result in rotation of the sectioning elements 124' around a central axis of the cutting member 120'. This rotation may facilitate uniform, or substantially uniform, severing of the distal end of a tissue sample.

In some embodiments, the spiral cut 140' and/or the sectioning elements 124' may rotate, or be configured to rotate, between 0° and plus or minus 90°. In some embodiments, the spiral cut 140' and/or the sectioning elements 124' may rotate, or be configured to rotate, between 0° and plus or minus 45°; between 0° and plus or minus 30°; between 0° and plus or minus 15°; between 0° and plus or minus 5°; or another suitable degree of rotation. Again, rotation of the sectioning elements 124' through a body tissue may form or result in a cleaner or sharper cut in a tissue sample, as rotation of the sectioning elements 124' may sever along a complete, or a substantially complete, circumference of the distal end of the tissue sample.

Figure 4A:
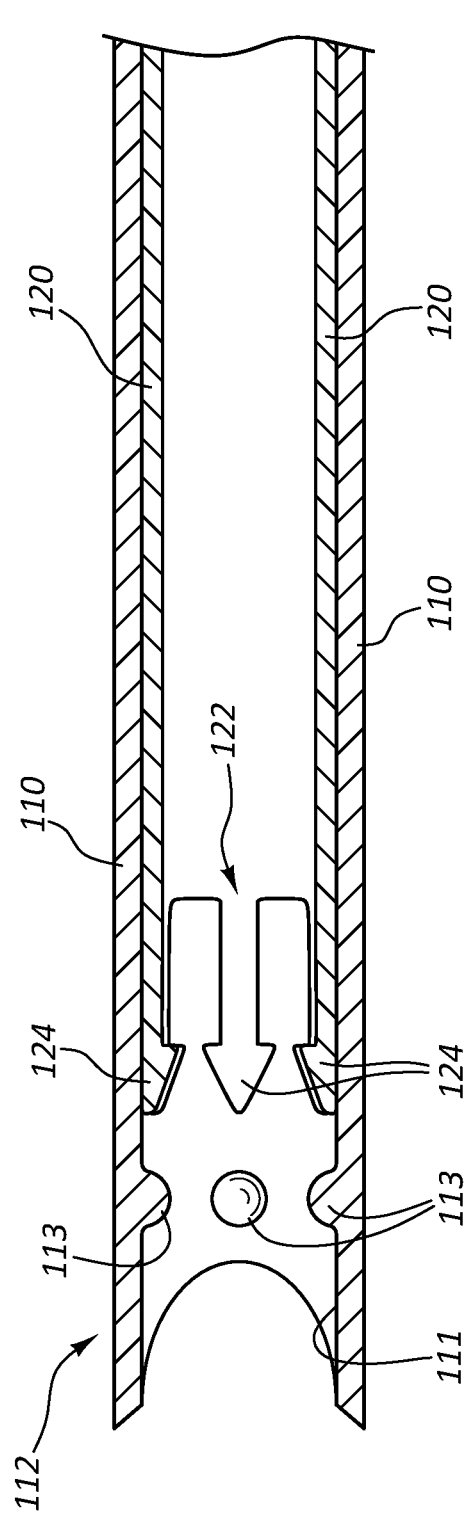
FIG. 4A is a cross-sectional view of portions of the outer tubular member and the cutting member of the biopsy needle assembly of FIGS. 1A and 1B in a first configuration.
Figure 4B:
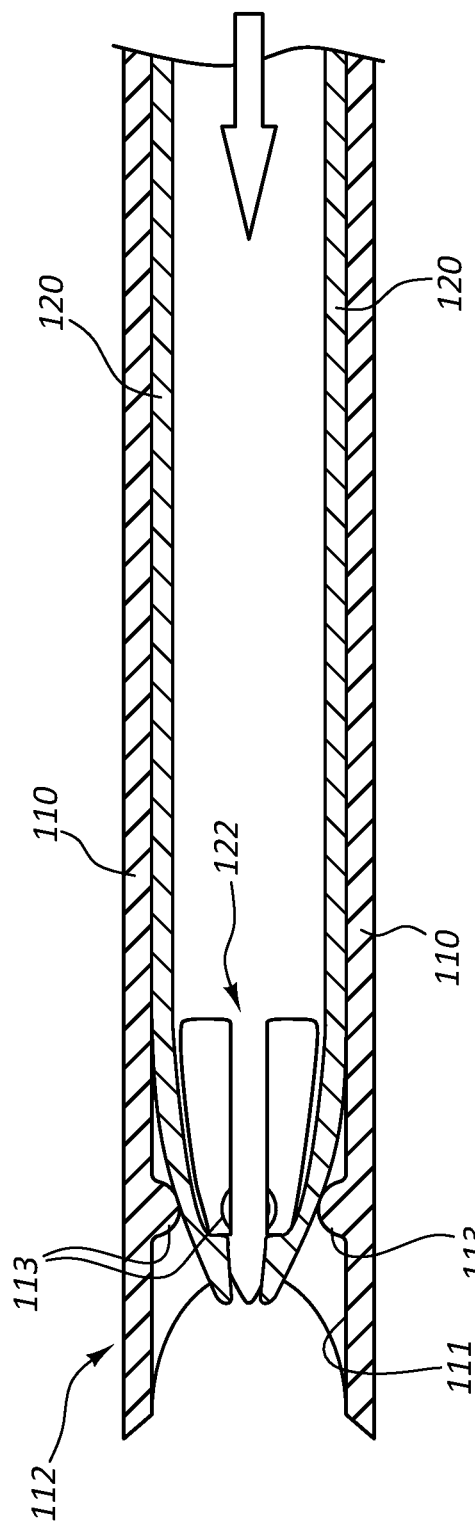
FIG. 4B is a cross-sectional view of the portions of the outer tubular member and the cutting member of the biopsy needle assembly of FIGS. 1A and 1B in a second configuration.

FIGS. 4A and 4B depict cross-sectional views of portions of the outer tubular member 110 and the cutting member 120 of FIGS. 1A and 1B in a first configuration and a second configuration, respectively. In FIG. 4A, at least a portion of the distal end portion 122 of the cutting member 120 is positioned proximal to at least a portion of the distal end portion 112 of the outer tubular member 110. In some embodiments, the outer tubular member 110 may be configured to displace a portion of at least one of the sectioning elements 124 of the cutting member 120 radially inward toward the central axis of the cutting member 120 in response to relative displacement of the outer tubular member 110 with respect to the cutting member 120. For example, as the cutting member 120 is moved distally relative to the outer tubular member 110, one or more of the sectioning elements 124 may interact with a portion of the outer tubular member 110 and be displaced inward toward the central axis of the cutting member 120.

As illustrated in FIGS. 4A and 4B, an inside surface 111 of at least a portion of the distal end portion 112 of the outer tubular member 110 can comprise a plurality of inwardly projecting protrusions 113. In some embodiments, the inside surface 111 of at least a portion of the distal end portion 112 of the outer tubular member 110 may comprise one or more inwardly projecting protrusions 113. In certain embodiments, the protrusions 113 may be configured to at least partially displace a portion of at least one of the sectioning elements 124 inward toward the central axis of the cutting member 120 when the cutting member 120 is displaced distally relative to the outer tubular member 110, as indicated by the arrow (FIG. 4B). As depicted in FIG. 4B, at least a portion of the distal end portion 122 of the cutting member 120 is positioned distal to at least a portion of the distal end portion 112 of the cutting member 110. The protrusions 113 can act to displace at least a portion of each of the sectioning elements 124 toward the central axis of the cutting member 120 when the cutting member 120 is displaced distally relative to the outer tubular member 110.

Other configurations of the outer tubular member 110, wherein the outer tubular member 110 is configured to inwardly displace at least a portion of the sectioning elements 124 of the cutting member 120 to cut or sever the second portion of the tissue sample are also within the scope of this disclosure. For example, the inside surface 111 of the distal end portion 112 of the outer tubular member 110 may comprise a raised, annular surface or ridge, such as a circular ridge extending completely around the inside diameter of the outer tubular member 110. In other embodiments, raised arc-shaped segments may also be utilized. The raised, annular surface or arc-shaped segments may be configured to displace a portion of at least one of the sectioning elements 124 inward toward the central axis of the cutting member 120 when the cutting member 120 is displaced distally relative to the outer tubular member 110. The raised, annular surface may also be configured to inwardly displace at least a portion of the sectioning elements 124 of the cutting member 120 to cut or sever the second portion of the tissue sample regardless of the relative rotations of the outer tubular member 110 and the cutting member 120 to each other.

In some embodiments, distal displacement of the cutting member 120 relative to the outer tubular member 110 may cause at least a portion of at least one of the sectioning elements 124 of the cutting member 120 to interact with a component of the outer tubular member 110 (including, but not limited to, the inwardly projecting protrusions 113, raised annular surface, or raised arc-shaped segments), displacing inward the at least one sectioning element 124 to sever at least a portion of the distal end, or second portion, of the tissue sample.

In certain embodiments, at least a portion of the outer tubular member 110, or the distal end portion 112 of the outer tubular member 110, may be configured to overlap one or more of the sectioning elements 124 of the cutting member 120, thus generating an overlapping arrangement. For example, the one or more sectioning elements 124 may be fully or substantially disposed within the outer tubular member 110. The overlapping arrangement of the outer tubular member 110 and the cutting member 120 can add rigidity and structure to at least a portion of the needle assembly. For example, the overlapping arrangement may reinforce the sectioning elements 124 and may reduce deformation of the sectioning elements 124 during use. For example, the outer tubular member 110, disposed around the sectioning elements 124, may prevent outward deformation of the sectioning elements 124 as the outer tubular member 110 and cutting member 120 are advanced through body tissue. Similarly, disposition of the cutting member 120 between the stylet and the outer tubular member 110 may tend to secure the sectioning elements 124, minimizing deformation thereof, as the needle assembly 105 is advanced through body tissue.

Further, the overlapping arrangement may also facilitate entry of body tissue into at least a portion of a lumen of the cutting member 120 without bending or otherwise damaging the one or more sectioning elements 124 and/or the cutting member 120. For example, the outer tubular member 110 may sever the first cylindrical portion of a tissue sample as the outer tubular member 110 is actuated. The cutting member 120 may generally follow the tube-like cut, or annular cut, created by the outer tubular member 110 as the cutting member 120 is initially advanced, prior to severing the second portion, or distal end, of the tissue sample. Thus, the relative position of the outer tubular member 110 with respect to the cutting member 120 may facilitate entry of the tissue sample into the lumen of the cutting member 120 without the tissue sample catching and prematurely deforming the sectioning elements 124. The tube-like path, or annular path, created by the tubular member 110 may also minimize or prevent body tissue from being blocked and/or damaged by the one or more sectioning elements 124 and/or the cutting member 120 when the body tissue enters the lumen of the cutting member 120. As described above, the outer tubular member 110 may be configured to generate a tube-like cut into a body tissue. In some embodiments, the overlapping arrangement may be configured such that the outer tubular member 110 directs the one or more sectioning elements 124 and/or the cutting member 120 into the body tissue at the site of the tube-like cut (for example, when a handle or actuator displaces or deflects the cutting member 120 into the body tissue). Such an arrangement may minimize or prevent the one or more sectioning elements 124 and/or the cutting member 120 from damaging the body tissue at or adjacent the tube-like cut, for example by minimizing the likelihood the tissue sample will be scratched or otherwise damaged as it passes the sectioning elements 124 and moves into the lumen of the cutting member 120.

Figure 5:
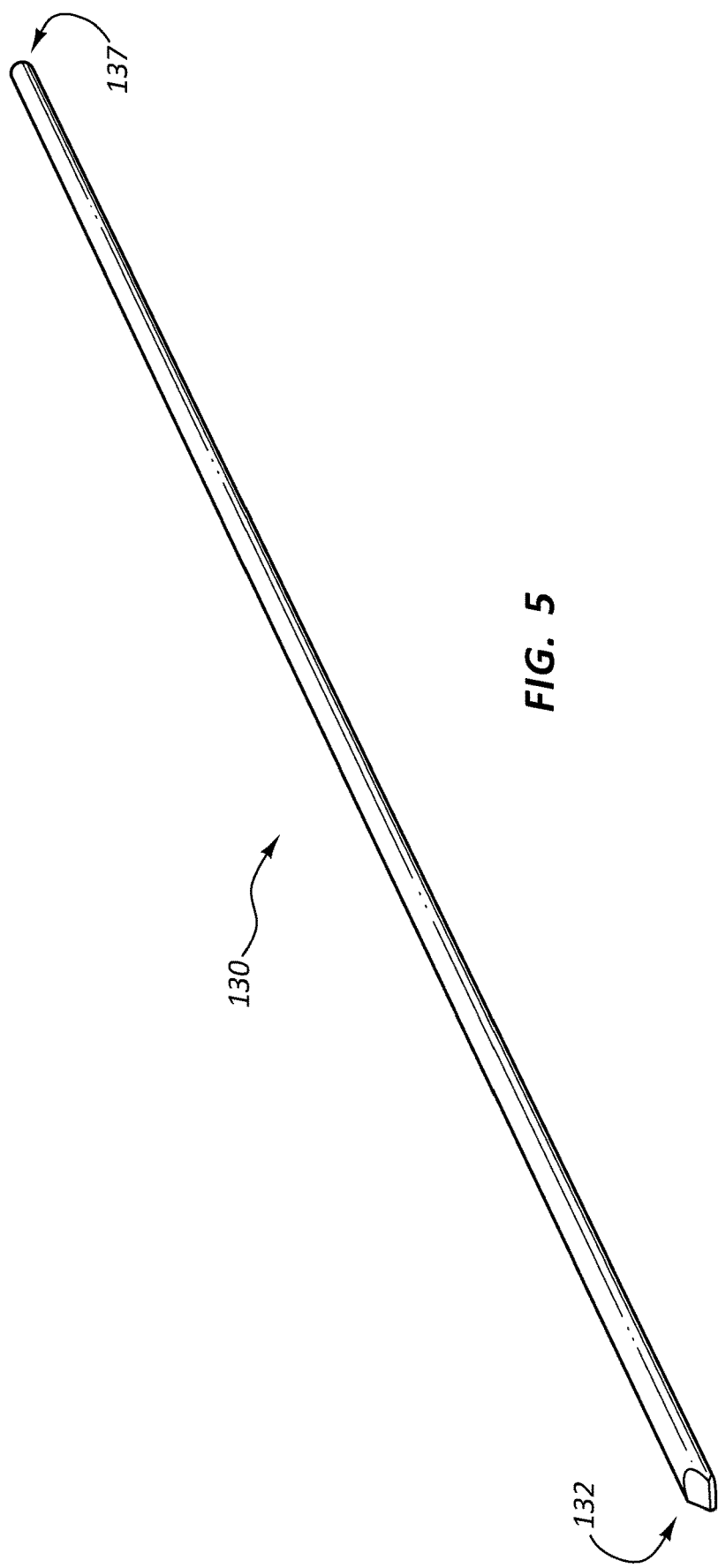
FIG. 5 is a perspective view of a stylet of the biopsy needle assembly of FIGS. 1A and 1B.

FIG. 5 is a perspective view of the stylet 130, or trocar, of the needle assembly 105 of FIG. 1A. The cutting member, as described above, may be slidably disposed around the stylet 130. In some embodiments, the stylet 130 may be fixed with respect to an actuator or handle as described below in connection with FIG. 6. Further, as depicted, the stylet 130 comprises the distal end portion 132 and a proximal end portion 137. The distal end portion 132, as illustrated, can be substantially sharp. In some embodiments, the stylet 130, and/or the distal end portion 132 of the stylet 130, may be configured to facilitate movement of the needle assembly through body tissue. For example, as described above, a practitioner or user can advance the stylet 130 through the skin and/or tissue of a patient to a position at or adjacent to the site of an identified tissue sample. As the stylet 130 is advanced, the stylet 130 may displace the skin and/or tissue such that a pathway is generated through the skin and/or tissue that may ease advancement of other components of the needle assembly to the position at or adjacent to the site of the tissue sample.

Figure 6:
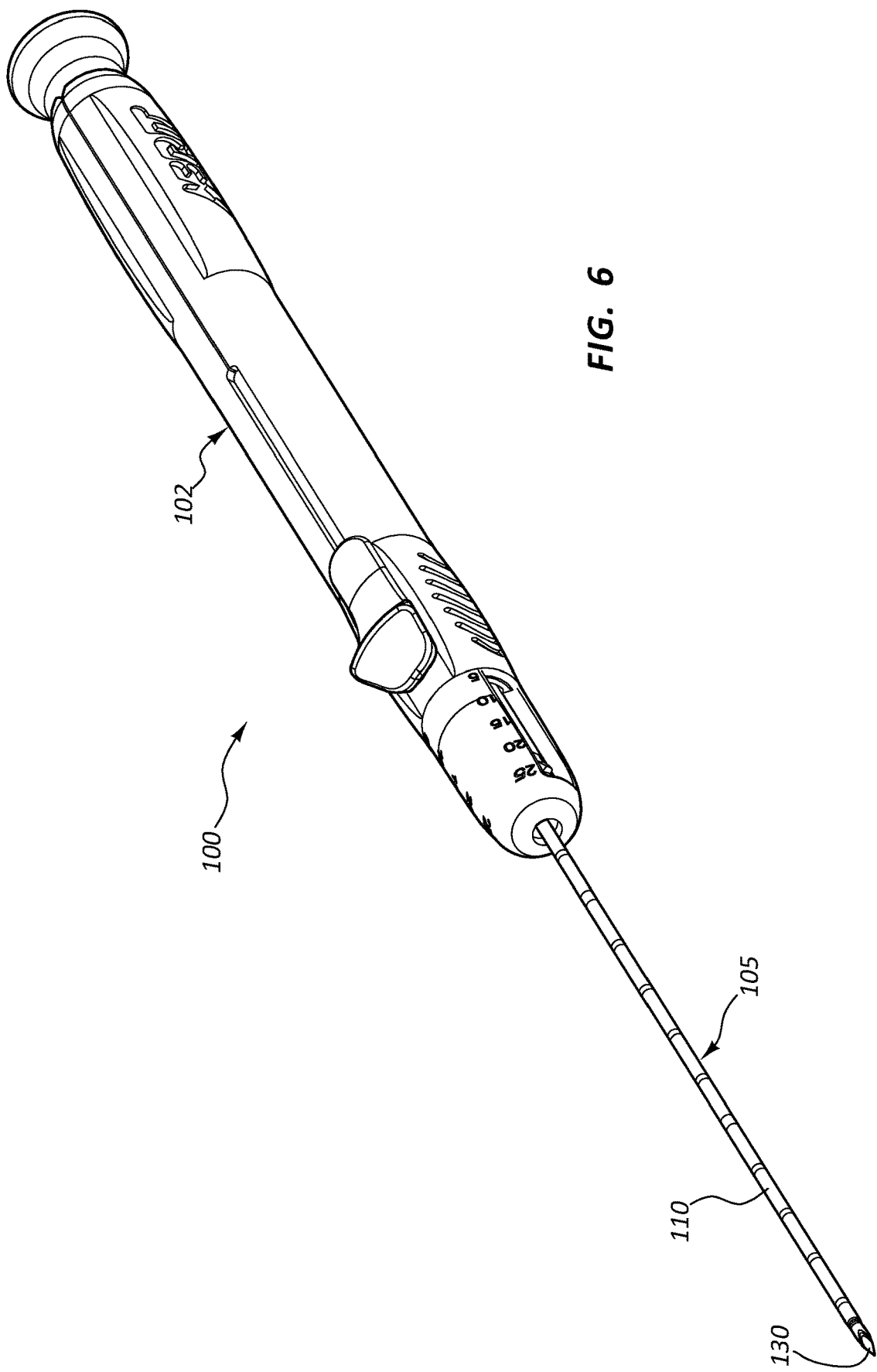
FIG. 6 is a perspective view of a tissue biopsy device comprising the biopsy needle assembly of FIGS. 1A and 1B.

FIG. 6 is a perspective view of a tissue biopsy device 100 comprising the needle assembly 105 of FIGS. 1A and 1B. The tissue biopsy device 100 can comprise a needle assembly 105 operatively coupled to a handle 102, or actuator. For example, at least a portion of at least one of the proximal end portions of the outer tubular member 110, the cutting member, and/or the stylet 130 may be operatively coupled to the handle 102. The handle 102 may be configured to actuate at least one of the outer tubular member 110, the cutting member, and/or the stylet 130 to cut or sever the tissue sample from the body of a patient. In some embodiments, the handle 102 may be configured to actuate at least the outer tubular member 110 and the cutting member to cut or sever the tissue sample from the body. The handle 102 may also be configured to retract the needle assembly 105 from the body and/or to extract the tissue sample from the body of a patient. It is within the scope of this disclosure to couple embodiments of the biopsy needle assembly, as described herein, to any type of handle or actuator. A handle or actuator can have springs and can displace components of the needle assembly 105 relative to each other. A series of steps or displacements of the components of the tissue biopsy device 100 can be effectuated in response to a single input or trigger by a practitioner. Various handles or actuators may be used with the biopsy needle assemblies disclosed herein. For example, U.S. patent application Ser. No. 14/157,935, filed on Jan. 17, 2014 and titled "Impact Biopsy Device and Method of Use," which is hereby incorporated by reference in its entirety, discloses handles and actuators that may be used in connection with the biopsy needle assemblies disclosed here.

Various tissue biopsy devices utilizing various components, as described above, and/or combinations of said components are also within the scope of this disclosure. For instance, an exemplary tissue biopsy device may comprise a first elongate member configured to be advanced into a body tissue, for example, an elongate member analogous to the stylet 130 of FIGS. 1A and 1B. The tissue biopsy device may further comprise a second elongate member, wherein the second elongate member is disposed around the first elongate member, and wherein the second elongate member is configured to sever a first portion of a tissue sample, for example, an elongate member analogous to the outer tubular member 110 of FIGS. 1A and 1B. Additionally, the tissue biopsy device may comprise a third elongate member, wherein the third elongate member may be movably disposed within the second elongate member and around the first elongate member, and wherein the third elongate member is configured to sever a second portion of the tissue sample at or adjacent a distal-most point of a distal end portion of the second elongate member, for example, an elongate member analogous to the cutting member 120 of FIG. 1B. In some embodiments, the third elongate member may be configured to cut or sever the second portion of the tissue sample at the same longitudinal position as the distal-most point of the distal end portion of the second elongate member. In other embodiments the third elongate member may be configured to cut or sever the second portion of the tissue sample at a position less than 5 mm, less than 4 mm, less than 3 mm, less than 2 mm, or less than 1 mm from the distal-most point of the distal end portion of the second elongate member. The third elongate member may also be configured to cut or sever the second portion of the tissue sample at other positions relative to the distal-most point of the distal end portion of the second elongate member. Further, the tissue biopsy device may comprise an actuator, for example, an actuator analogous to the handle 102 of FIG. 6. The actuator may be configured to displace or deflect at least one of the second elongate member and the third elongate member such that the tissue sample is severed. The actuator may also be configured to retract each of the first elongate member, the second elongate member, the third elongate member, and/or the tissue sample from the body of a patient.

In some embodiments, a distal end portion of the third elongate member is configured to contract toward a central axis of the third elongate member to sever the second portion of the tissue sample. In certain embodiments, the distal end portion of the second elongate member may be configured to deflect the contraction of the distal end portion of the third elongate member. The third elongate member can also be configured to extract the severed tissue sample from the body tissue and/or the patient.

Figure 7A:
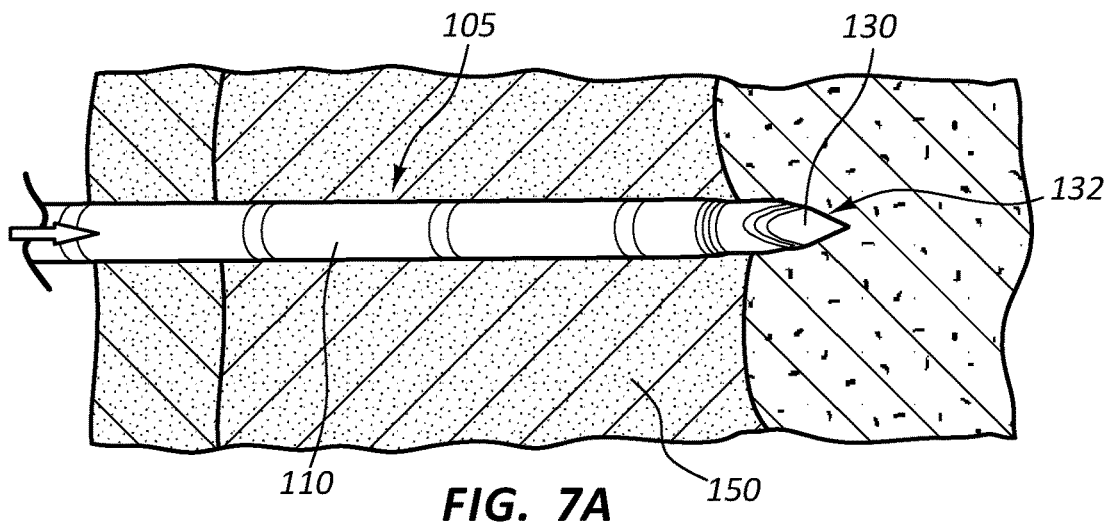
FIG. 7A is a schematic representation of portions of the outer tubular member, the cutting member, and the stylet of the biopsy needle assembly of FIGS. 1A and 1B in a first configuration.
Figure 7B:
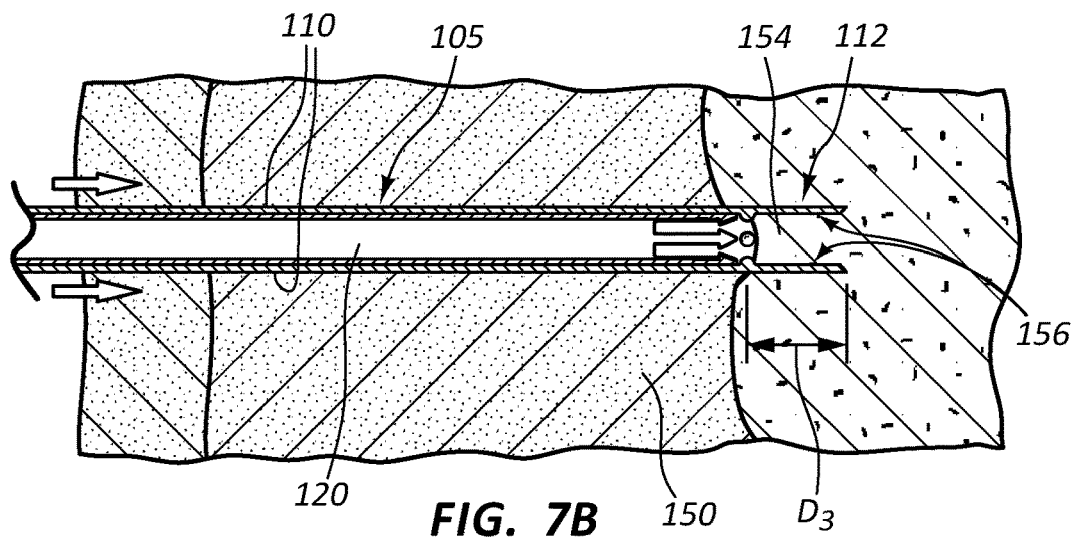
FIG. 7B is a schematic cross-sectional representation of the portions of the outer tubular member and the cutting member of the biopsy needle assembly of FIG. 7A in a second configuration.
Figure 7C:
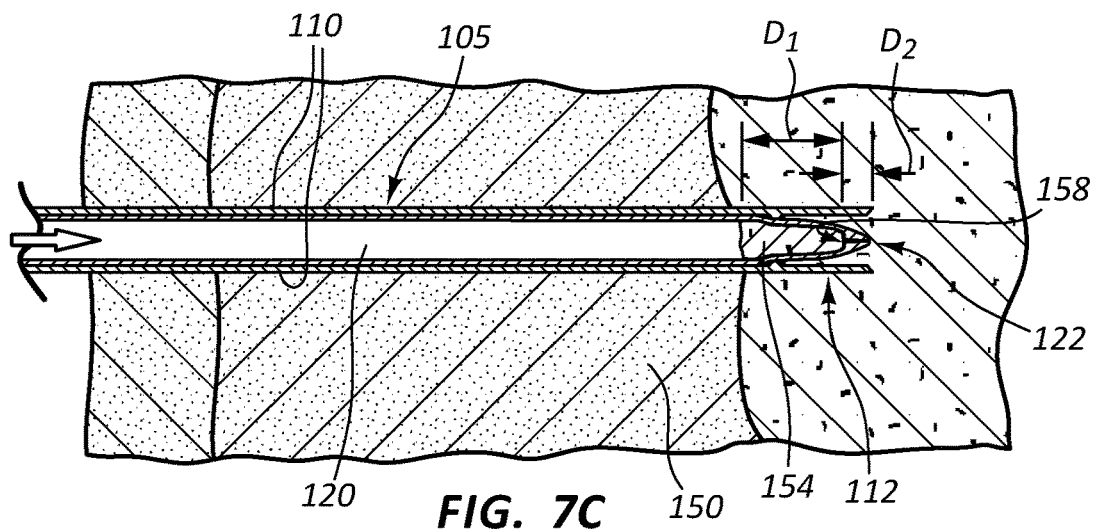
FIG. 7C is a schematic cross-sectional representation of the portions of the outer tubular member and the cutting member of the biopsy needle assembly of FIG. 7A in a third configuration.

FIGS. 7A-7C are schematic in nature. In other words, the figures show the functional and operational relationships of a portion of the biopsy needle assembly 105 upon use in a patient, but the figures are not intended to indicate any particular structure or spatial disposition of any tissue, organ, body component, or group of body components in the patient. Additionally, the schematic representations herein may be drawn to show internal tissues and/or organs of the patient without explicitly designating cross-sections or cutaways of the tissues and/or organs. For example, a body tissue may be schematically shown with the biopsy needle assembly disposed therein without indicating a cross-section portion or cutaway of a portion of the body tissue. FIG. 7A is a schematic representation of a side view of a portion of the needle assembly 105 of FIG. 1A in a first configuration. FIGS. 7B and 7C are schematic representations of cross-sectional views of the portion of the needle assembly 105 of FIG. 7A in a second configuration and a third configuration, respectively. For clarity, the stylet 130 of FIG. 1A is not shown in FIGS. 7B and 7C.

FIG. 7A illustrates at least the outer tubular member 110 and the stylet 130 of the needle assembly 105 advanced into a body tissue 150, as shown by the arrow. In some embodiments, a practitioner may determine a tissue sample to obtain. As such, the distal end portion 132 of the stylet 130 may be disposed to a position at or adjacent a proximal end portion of the predetermined tissue sample. Referring to FIG. 7B, displacement of the outer tubular member 110 with respect to the cutting member 120 and the body tissue 150 is depicted, as shown by the arrows. As depicted, such displacement of the outer tubular member 110, and the distal end 112 of the outer tubular member 110, can sever a first portion 156 of a tissue sample 154. In some embodiments, the distal end portion 112 of the outer tubular member 110 can be displaced distally relative to the distal end portion of the stylet (not shown), such that the distal end portion 112 of the outer tubular member 110 is extended a distance, or stroke length, into the body tissue 150 relative to the stylet. The length $D_3$, as identified in FIG. 7B, represents the stroke length, as described above.

Referring to FIG. 7C, the distal end portion 122 of the cutting member 120 may be displaced, as shown by the arrow, to a position at or adjacent the distal end portion 112 of the outer tubular member 110. Displacement of the cutting member 120 with respect to the outer tubular member 110 and the body tissue 150 may result in at least a portion of the cutting member 120 severing a second portion 158 of the tissue sample 154 at or adjacent a distal-most point of the distal end portion 112 of the outer tubular member 110. For example, the cutting member 120 may be configured to cut or sever the second portion 158 of the tissue sample 154 at a position less than 5 mm, less than 4 mm, less than 3 mm, less than 2 mm, or less than 1 mm from the distal-most point of the distal end portion 112 of the outer tubular member 110. The cutting member 120 may also be configured to cut or sever the second portion 158 of the tissue sample 154 at the same longitudinal position as the distal-most point of the distal end portion 112 of the outer tubular member 110. The cutting member 120 may also be configured to cut or sever the second portion 158 of the tissue sample 154 at other positions relative to the distal-most point of the distal end portion 112 of the outer tubular member 110.

The length $D_1$, as depicted in FIG. 7C, represents the length of the severed tissue sample 154, or tissue sample length. The length $D_2$, as depicted, represents the length of the dead space, as described above. In some embodiments of the present disclosure, the configuration of the distal end portion 122 of the cutting member 120 with respect to the distal end portion 112 of the outer tubular member 110 may be such that the distal end of the tissue sample 154 is severed at or adjacent the distal end portion 112 of the outer tubular member 110. Such a configuration may minimize or eliminate the length of the dead space. In certain configurations, the distal end portion 122 of the cutting member 120 can engage with at least a portion of the distal end portion 112 of the outer tubular member 110 such that the distal end portion 122 of the cutting member 120 is configured to sever the second portion 158 of the tissue sample 154. In various embodiments, as described above, severing the second portion 158 of the tissue sample 154 may comprise displacing at least a portion of the distal end portion 122 of the cutting member 120 toward a central axis of the cutting member 120.

As described, the tissue sample length $D_1$ and the dead space length $D_2$ are equal, or approximately equal, to the stroke length $D_3$ (i.e., $D_1+D_2 \approx D_3$). In at least some embodiments of the needle assembly of the present disclosure, the needle assembly is configured to minimize or eliminate the length of the dead space $D_2$. As such, in said embodiments the tissue sample length $D_1$ may be equal, or approximately equal, to the stroke length $D_3$ (i.e., $D_1 \approx D_3$). Such embodiments of biopsy needle assemblies, as described above, may be configured for use when it may be undesirable to cut, pierce, or sever a body component, tissue, or sample at or adjacent a predetermined tissue sample or simply to minimize trauma to surrounding tissue during a biopsy.

In some embodiments, actuation of the outer tubular member 110 and/or the cutting member 120 may be effectuated by a handle or actuator, such as handle 102 of FIG. 6. In certain embodiments, displacement of the outer tubular member 110 may occur prior to the displacement of the cutting member 120. In certain other embodiments, displacement of the outer tubular member 110 and the cutting member 120 may occur substantially simultaneously. The position of the stylet may remain substantially stationary during the displacement of each of the outer tubular member 110 and the cutting member 120. Other timing and/or sequences of the displacement of each of the outer tubular member 110 and the cutting member 120 are also contemplated.

Upon severing of the tissue sample 154, as illustrated in FIG. 7C, each of the stylet, the outer tubular member 110, and the cutting member 120 may be retracted from the body tissue 150 of the patient such that the tissue sample 154 can be extracted from the body tissue 150. In certain embodiments, relative positions of each of the stylet, the outer tubular member 110, and the cutting member 120 may be substantially maintained upon the retraction of the each of the stylet, the outer tubular member 110, and the cutting member 120 from the body tissue 150.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art, and having the benefit of this disclosure, that changes may be made to the details of the above-described embodiments without departing from the underlying principles of the disclosure herein.

The invention claimed is:

1. A biopsy needle assembly configured for use with a tissue biopsy device, the biopsy needle assembly comprising:
   a linear outer tubular member comprising a distal end portion configured to sever a first portion of a tissue sample; and
   a cutting member slidably disposed within the linear outer tubular member, wherein the cutting member comprises a distal end portion, and wherein the distal end portion of the cutting member is configured to displace inward to sever a second portion of the tissue sample; and
   an actuator configured to displace the cutting member relative to the linear outer tubular member,
   wherein the distal end portion of the cutting member further comprises one or more sectioning elements, and wherein displacement of a portion of at least one of the sectioning elements toward a central axis of the cutting member is configured to sever the second portion of the tissue sample,
   wherein the cutting member further comprises a spiral cut disposed proximal of the one or more sectioning elements, wherein the spiral cut is a single continuous smooth spiral cut, wherein the spiral cut is configured to longitudinally compress during actuation of the actuator of the biopsy needle assembly, and
   wherein the spiral cut is configured to rotate the one or more sectioning elements around the central axis of the cutting member relative to a proximal end portion of the cutting member an amount between one degree and 15 degrees when the spiral cut is compressed from an uncompressed state to a compressed state.

2. The biopsy needle assembly of claim 1, wherein the linear outer tubular member is configured to displace the portion of the at least one of the sectioning elements toward the central axis of the cutting member in response to relative displacement of the linear outer tubular member in relation to the cutting member caused by the actuation of the actuator of the biopsy needle assembly.

3. The biopsy needle assembly of claim 2, wherein an inside surface of the distal end portion of the linear outer tubular member comprises one or more inwardly projecting protrusions, and wherein the one or more protrusions are configured to displace the portion of the at least one of the sectioning elements inward toward the central axis of the cutting member when the cutting member is displaced distally relative to the linear outer tubular member caused by the actuation of the actuator of the biopsy needle assembly.

4. The biopsy needle assembly of claim 1, wherein the portion of the at least one of the sectioning elements is elastically deformable inward toward the central axis of the cutting member.

5. The biopsy needle assembly of claim 1, wherein the cutting member is configured to sever the second portion of the tissue sample at or adjacent a distal-most point of the distal end portion of the linear outer tubular member.

6. The biopsy needle assembly of claim 1 wherein the cutting member is configured to sever the second portion of the tissue sample at a position less than 3 mm from a distal-most point of the distal end portion of the linear outer tubular member.

7. The biopsy needle assembly of claim 1, further comprising a stylet disposed within the cutting member, wherein the stylet comprises a distal end portion configured to facilitate advancement of the biopsy needle assembly through a body tissue.

8. The biopsy needle assembly of claim 1, wherein the spiral cut is configured to compress evenly laterally.

9. The biopsy needle assembly of claim 1, wherein the spiral cut is configured to compress evenly longitudinally.

10. The biopsy needle assembly of claim 1, wherein the linear outer tubular member extends from a proximal end to a distal end of a longitudinal axis.

11. The biopsy needle assembly of claim 1, wherein the one or more sectioning elements comprise a serrated lateral surface.

12. A tissue biopsy device configured to obtain a tissue sample, comprising:
    a first elongate member configured to be advanced into a body tissue;
    a second elongate member movably disposed around the first elongate member and configured to sever a first portion of the tissue sample, wherein the second elongate member extends from a proximal terminal end to a distal terminal end along a longitudinal axis;
    a third elongate member movably disposed within the second elongate member and configured to sever a second portion of the tissue sample at or adjacent a distal-most point of the distal terminal end of the second elongate member;
    wherein the third elongate member further comprises a spiral cut, wherein the spiral cut is configured to longitudinally compress during actuation of the tissue biopsy device; and
    wherein the third elongate member is configured such that axial movement of a proximal terminal end of the third elongate member causes the spiral cut to compress, and
    wherein upon compression from an uncompressed state to a compressed state a distal terminal end of the third elongate member is configured to rotate around a central axis of the third elongate member an amount between one degree and 15 degrees with respect to the proximal terminal end of the third elongate member; and
    an actuator configured to actuate at least the biopsy device to displace the second elongate member relative to the third elongate member such that at least the second portion of the tissue sample is severed.

13. The device of claim 12, wherein a distal end portion of the third elongate member is configured to contract toward the central axis of the third elongate member to sever the second portion of the tissue sample.

14. The device of claim 13, wherein a distal end portion of the second elongate member is configured to deflect the contraction of the distal end portion of the third elongate member.

15. The device of claim 12, wherein the third elongate member is further configured to extract at least a portion of the second portion of the tissue sample from the body tissue.

16. A method of obtaining a tissue sample, comprising:
    advancing a stylet into a body tissue;
    displacing a linear outer tubular member with respect to the stylet such that a distal end portion of the linear outer tubular member severs a first portion of the tissue sample; and
    displacing a cutting member with respect to the linear outer tubular member such that the cutting member severs a second portion of the tissue sample at or adjacent a distal-most point of the distal end portion of the linear outer tubular member,
    wherein the cutting member further comprises a spiral cut, wherein the spiral cut is configured to longitudinally compress during the displacement of the cutting member,
    wherein axial movement of a proximal terminal end of the cutting member causes the spiral cut to compress, and
    wherein upon compression from an uncompressed state to a compressed state a distal terminal end of the cutting member rotates between one degree and 15 degrees with respect to the proximal terminal end of the cutting member, and
    wherein the tissue sample comprises the first portion of the tissue sample and the second portion of the tissue sample.

17. The method of claim 16, wherein the advancing the stylet into the body tissue further comprises:
    determining the tissue sample to obtain; and
    disposing a distal end portion of the stylet to a position at or adjacent a proximal end portion of the tissue sample.

18. The method of claim 16, wherein the displacing the linear outer tubular member with respect to the stylet further comprises displacing the distal end portion of the linear outer tubular member distally relative to a distal end portion of the stylet such that the distal end portion of the linear outer tubular member is disposed a predetermined distance into the body tissue.

19. The method of claim 16, wherein the displacing the cutting member with respect to the linear outer tubular member further comprises displacing a distal end portion of the cutting member to a position at or adjacent the distal end portion of the linear outer tubular member.

20. The method of claim 16, wherein the displacing the cutting member with respect to the linear outer tubular member further comprises engaging a distal end portion of the cutting member with the distal end portion of the linear outer tubular member such that the distal end portion of the cutting member is configured to sever the second portion of the tissue sample.

21. The method of claim 16, wherein severing the second portion of the tissue sample comprises displacing at least a portion of a distal end portion of the cutting member toward a central axis of the cutting member.

22. The method of claim 16, further comprising retracting each of the stylet, the linear outer tubular member, and the cutting member from the body tissue such that at least the second portion of the tissue sample is extracted from the body tissue, wherein relative positions of each of the stylet, the linear outer tubular member, and the cutting member are maintained upon the retraction.

\* \* \* \* \*